United States Patent

Ichikawa et al.

[11] 3,978,092
[45] Aug. 31, 1976

[54] PROCESS FOR THE PREPARATION OF UNSATURATED CARBONYL COMPOUNDS

[75] Inventors: Yataro Ichikawa; Mamoru Yamamoto, both of Iwakuni, Japan

[73] Assignee: Teijin Limited, Osaka, Japan

[22] Filed: May 6, 1974

[21] Appl. No.: 467,618

[30] Foreign Application Priority Data

May 14, 1973 Japan.............................. 48-52630
May 15, 1973 Japan.............................. 48-53186
Oct. 4, 1973 Japan............................. 48-110947

[52] U.S. Cl.................... 260/347.8; 260/598; 260/599; 260/601 R; 260/611 R; 260/611 A; 260/611 F; 260/614 R; 260/494; 260/488 R

[51] Int. Cl.²............... C07D 307/46; C07C 47/20; C07C 47/45

[58] Field of Search................ 260/347.8, 601, 599, 260/611, 614, 598

[56] References Cited
UNITED STATES PATENTS 2,501,144   3/1950   Saunders.......................... 260/601

*Primary Examiner*—Harry I. Moatz
*Attorney, Agent, or Firm*—Sherman & Shalloway

[57] ABSTRACT

An unsaturated carbonyl compound, for example, one expressed by the following formula

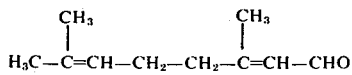

is prepared by maintaining at an elevated temperature an allyl acetal of an α,β-unsaturated aldehyde, for example, one expressed by the following formula

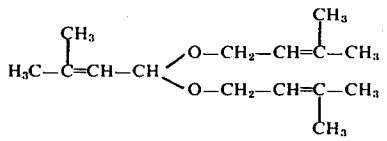

or a novel dienyl ether derived from it, for example, one expressed by the following formula

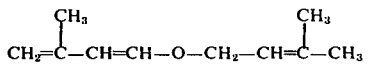

The allyl acetal can be derived, for example, from β-methylcrotonaldehyde having 5 carbon atoms and prenyl alcohol having 5 carbon atoms. It is possible therefore to introduce an allyl residue containing at least 3 carbon atoms into the carbon atoms at the γ-position to the carbonyl group of an α,β-unsaturated aldehyde containing at least 5 carbon atoms by a reaction consisting of the reduced number of steps. Moreover, the unsaturated aldehyde having the increased number of carbon atoms can be formed at a high yield by a relatively simple reaction.

13 Claims, No Drawings

PROCESS FOR THE PREPARATION OF UNSATURATED CARBONYL COMPOUNDS

This invention relates to a process for the preparation of unsaturated carbonyl compounds. More particularly, the invention relates to a process for the preparation of unsaturated carbonyl compounds from allylacetal derivatives derived from $\alpha,\beta$-unsaturated aldehyde, or from the dienyl ethers derivable further from said allylacetal derivatives.

The invention furthermore relates to the novel dienyl ethers and a process for their preparation.

The novel dienyl ethers provided by the present invention are the important intermediate product formed in the course of making unsaturated carbonyl compounds, whereas the unsaturated carbonyl compounds are known to be useful in the art of terpene chemical industries. Particularly they are industrially valuable compounds as perfume, medicines, pesticides, or as the intermediates thereof.

Such unsaturated carbonyl compounds have been heretofore prepared through cumbersome procedures. For example, carbonyl compounds and acetylene are first used to form acetylene alcohols which are then reduced to the corresponding alcohols, and the alcohols are reacted with diketene, acetoacetic ester, isopropenyl ether, or the like (U.S. Pat. No. 2516826, 2628250, 2638484).

Such conventional process requires a large number of reaction steps because, for example, five carbon atoms are to be added to the starting carbonyl compound. Furthermore, the use of acetylene, which is difficult to handle, as the reactant inevitably renders the process industrially disadvantageous.

Again, U.S. Pat. No. 2,501,144 teaches a process of heating the diallylacetal of the formula A-1 below,

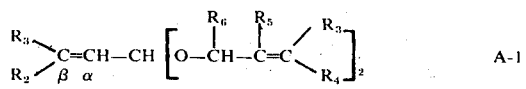

in which $R_1$, $R_2$, $R_3$, $R_4$, $R_4$, and $R_6$ are each selected from alkyl groups of 1 – 4 carbons,
to a temperature from 150° to 300°C., whereby producing the unsaturated aldehyde of formula A-2,

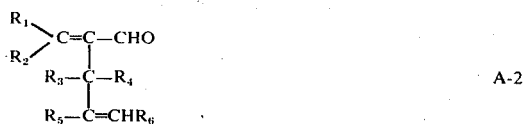

in which $R_1$ through $R_6$ have the above-given definitions. However, the above reaction product is entirely different from that intended by the invention as will be described later, in that the prior art reaction
a. introduces allyl group to the carbon atom at the $\alpha$-position to the carbonyl group

of unsaturated aldehyde, and furthermore,
b. the allyl group is introduced as the carbon atom at the $\alpha$-position to the hydroxyl group of allyl alcohol is bonded with the carbon atom at the $\alpha$-position to the carbonyl group of the unsaturated aldehyde.

Also Mr. Alan F. Thomas disclosed his views in Journal of the American Chemical Society, Vol. 91, No. 12, 3281 — 3289 (1969), that the reaction of the allyl alcohol derivatives of formula (B-1) below with the dienyl ether of formula (B-2),

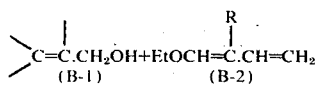

to form the unsaturated aldehyde of the following formula (B-3)

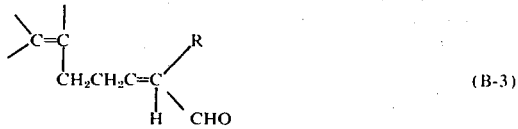

progresses only when the carbon atom at the $\alpha$-position to the ether group

of the dienyl ether is substituted by, for example, a methyl group ($-CH_3$), but fails to progress if the $\alpha$-positioned carbon atom is substituted with a hydrogen atom.

German Patent Application, Publication No. 2,157,035 printed on May 24, 1973 discloses, on the other hand, a method of reacting allyl alcohol derivatives such as 3-methyl-2-butene-1-ol with an unsaturated aldehyde such as 3,3-dimethylacrolein in a liquid phase at elevated temperatures, whereby forming an unsaturated aldehyde such as citral through a single-stage reaction.

In contrast thereto, according to the present invention, unsaturated aldehyde is formed from the allylacetal of formula (I), shown below, or from the dienyl ether of formula (III), also shown below. Furthermore, according to the subject process in passing through the intermediate stage of such allylacetal (I) or dienyl ether (III), the unsaturated aldehyde is obtained at higher conversion and selectivity.

According to the present invention, the allylacetal derivatives of formula (I) shown below:

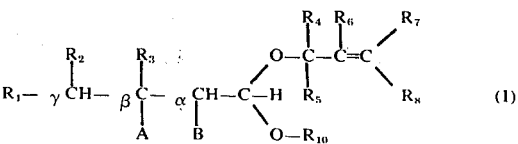

in which
$R_1$ and $R_2$ may be the same or different, each denoting hydrogen or an organic group which is inert to the reaction,
$R_3$ is an organic group inert to the reaction,
A and B are the groups which may be together forming a double bond between the carbons at $\alpha$- and $\beta$-positions, or may form a double bond as eliminated, $R_4$, $R_5$, $R_6$, $R_7$ and $R_8$ may be the same or different, each denoting a hydrogen atom or an organic group which is inert to the reaction, and $R_{10}$ stands for a hydrogen atom, an organic group, or a carboxylic acid residue, are heated to be converted to the unsaturated carbonyl compounds of formula (II)

$$\underset{R_8}{\overset{R_7}{\diagdown}}C=\underset{R_5}{\overset{R_6}{C}}-\underset{R_2}{\overset{R_4}{C}}-\underset{}{\overset{R_1}{C}}-\overset{R_3}{C}=CH-\overset{H}{\underset{}{C}}=O \quad (II)$$

in which $R_1$, $R_2$, $R_3$, $R_4$, $R_5$, $R_6$, $R_7$ and $R_8$ have the same definitions as those given with the above formula (I).

According to our studies, it is confirmed that when the allylacetal derivatives of formula (I) are heated, they are converted to the dienyl ether derivatives of formula (III):

$$R_1-\overset{R_2}{\underset{}{C}}=\overset{R_3}{\underset{}{C}}-CH=\overset{H}{\underset{}{C}}-O-\underset{R_5}{\overset{R_4}{C}}-\overset{R_6}{C}=C\underset{R_8}{\overset{R_7}{\diagdown}} \quad (III)$$

in which $R_1$, $R_2$, $R_3$, $R_4$, $R_5$, $R_6$, $R_7$ and $R_8$ have the previously given definitions as to formula (I), and then further rearranged to form the unsaturated carbonyl compounds of formula (II).

The unsaturated carbonyl compounds of formula (II), therefore, can also be prepared by using the above dienyl ether derivatives of formula (III) as the starting material. The dienyl ether derivatives of formula (III) are the novel compounds never disclosed in the literature to date, but first synthesized by the present inventors.

The allylacetal derivatives of formula (I), which are used as one of the starting materials according to the invention, can be formed from, for example, the corresponding α,β-unsaturated carbonyl compounds or compounds capable of forming such (precursors), and the corresponding allyl alcohol. Therefore, as can be understood from the above-listed formula (II), it is possible according to the invention to introduce the hydrocarbon residue of an allyl alcohol, to the carbon atom located at the α-position to the carbonyl group in the α,β-unsaturated carbonyl compound or a compound convertible to such an unsaturated carbonyl compound.

Furthermore, the invention is highly advantageous in that according to the subject process, the unsaturated carbonyl compounds (formula II) can be formed from the allylacetal derivatives (formula I) or the dienyl ether derivatives (formula III) with extremely high conversion and selectivity.

Hereinafter the invention will be explained in further details. [I] Allylacetal derivatives (I) and their preparation:

[I-1] Allylacetals (I)

The allylacetal derivatives of formula (I)

$$R_1-CH-\underset{\underset{B}{|}}{\overset{\overset{A}{|}}{C}}-CH-C\underset{O-R_{10}}{\overset{O-\underset{R_5}{\overset{R_4}{C}}-\overset{R_6}{C}=C\underset{R_8}{\overset{R_7}{\diagdown}}}{\diagup}}\overset{}{\underset{H}{\diagdown}} \quad (I)$$

in which $R_1$, $R_2$, $R_3$, $R_4$, $R_5$, $R_6$, $R_7$, $R_8$, $R_{10}$, A, and B have the previously given definitions, which are used as one of the starting materials according to the invention may belong to any of the below-identified groups of compounds (Ia), (Ib), and (Ic).

$$R_1-CH-\underset{\underset{B}{|}}{\overset{\overset{A}{|}}{C}}-CH-C\underset{O-\underset{R_5}{\overset{R_4}{C}}-\overset{R_6}{C}=C\underset{R_8}{\overset{R_7}{\diagdown}}}{\overset{O-\underset{R_5}{\overset{R_4}{C}}-\overset{R_6}{C}=C\underset{R_8}{\overset{R_7}{\diagdown}}}{\diagup}}\overset{H}{\underset{}{}} \quad (Ia)$$

$$R_1-CH-\underset{\underset{B}{|}}{\overset{\overset{A}{|}}{C}}-CH-C\underset{O-R_{11}}{\overset{O-\underset{R_5}{\overset{R_4}{C}}-\overset{R_6}{C}=C\underset{R_8}{\overset{R_7}{\diagdown}}}{\diagup}}\overset{H}{\underset{}{}} \quad (Ib)$$

$$R_1-CH-\underset{\underset{B}{|}}{\overset{\overset{A}{|}}{C}}-CH-C\underset{O-\underset{O}{\overset{}{C}}-R_{12}}{\overset{O-\underset{R_5}{\overset{R_4}{C}}-\overset{R_6}{C}=C\underset{R_8}{\overset{R_7}{\diagdown}}}{\diagup}}\overset{H}{\underset{}{}} \quad (Ic)$$

In the foregoing formulae (Ia), (Ib), and (Ic), $R_1$, $R_2$, $R_3$, $R_4$, $R_5$, $R_6$, $R_7$, $R_8$, A, and B have the previously given definitions, $R_{11}$ in formula (Ib) is an organic group, and $R_{12}$ in formula (Ic) is a hydrocarbon residue.

Of the above three groups, the diallylacetal derivatives of formula (Ia) are particularly suitable as the starting material for the subject process.

[I-2] Preparation of allylacetals (Ia), (Ib), and (Ic):

A. The diallylacetal derivatives of formula (Ia) can be formed by reacting, for example, an unsaturated carbonyl compound of formula (IV), $$R_1-CH-\underset{\underset{B}{|}}{\overset{\overset{A}{|}}{C}}-CH-C\underset{\diagdown O}{\overset{\diagup H}{}} \quad (IV)$$

in which $R_1$, $R_2$, $R_3$, A, and B have the previously given definitions, or a compound convertible to the unsaturated carbonyl compound (precursor) with at least 2 molar times thereof of an allyl alcohol of formula (V), $$R_9O-\underset{R_5}{\overset{R_4}{C}}-\overset{R_6}{C}=C\underset{R_8}{\overset{R_7}{\diagdown}} \quad (V)$$

in which $R_4$, $R_5$, $R_6$, $R_7$ and $R_8$ have the previously given definitions, preferably in the presence of a suitable catalyst, e.g., an acid catalyst. Normally the reaction is advantageously performed by using an excess of allyl alcohol (formula V), for example, 4 molar times or more, to the unsaturated carbonyl compound of formula (IV) or a precursor thereof. The reaction can be performed, for example, at 80° – 110°C., preferably in the presence of an acid catalyst such as ammonium sulfate, ammonium nitrate, boric acid, oxalic acid, ammonium salt of p-toluenesulfonic acid, zinc chloride, aluminum chloride, or the like, under the conditions which will secure good dewatering from the reaction system. The reaction is normally performed at atmospheric or reduced pressure with advantage.

(B-1) The allylacetal derivatives of formula (Ib) may be formed through the steps of reacting, for example, the unsaturated carbonyl compound of formula (IV) with the alcohols of formula (VIa):

$$HOR_{11} \qquad (VIa)$$

in which
  $R_{11}$ has the previously given definition, under the conditions similar to those described in the preparation of allylacetals of formula (Ia) above, to form the acetal of formula (Ib'),

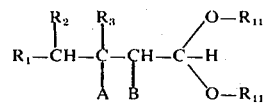

(Ib')

in which
  $R_1$, $R_2$, $R_3$, $R_{11}$, A, and B have the previously given definitions,
and then further reacting the diacetal with an equimolar or less amount of the allyl alcohol of formula (V) to effect an alcohol-exchange reaction while distilling the alcohol of formula (VIa) off from the system.

C. The allylacetal of formula (Ib) may also be formed by reacting the unsaturated carbonyl compound of formula (IV) or a precursor thereof with a mixture of the allyl alcohol of formula (V) and the alcohol of formula (VIa) at a suitable ratio. As the reaction conditions, those described in the preparation of the allylacetal of formula (Ia) are likewise applicable.

D. Again, the diallylacetal derivatives of formula (Ia) may be formed by further reacting the allylacetals of formula (Ib) with the allyl alcohol of formula (V) to effect an alcohol-exchange reaction.

(B-2) The acetals of the foregoing formula (Ib') may also be formed by, for example, reacting the unsaturated carbonyl compound of formula (IV) or a precursor thereof, with ortho-formate of formula (VIb):

$$HC(OR_{11})_3 \qquad (VIb)$$

in which $R_{11}$ has the already given definition.

(E-1) The allylacetals of formula (Ic) can be prepared by reacting the unsaturated carbonyl compound of formula (IV) with, for example, the carboxylic anhydride of formula (VIc);

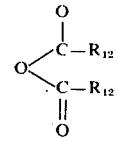

(VIc)

in which
  $R_{12}$ has the already given definition, to form a dicarboxylate of formula (Ic');

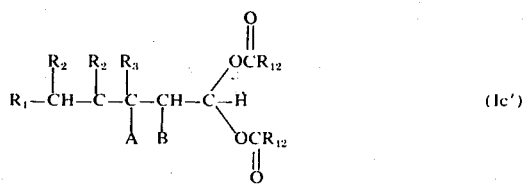

(Ic')

in which
  $R_1$, $R_2$, $R_3$, $R_{12}$, A, and B have the already given definitions,
and then reacting the dicarboxylate with a suitable amount of the allyl alcohol of formula (V). Obviously, the above reaction may be utilized for making the diallylacetals of formula (Ia).

(E-2) In the above reaction for making the dicarboxylate (Ic'), it is advantageous to use a relatively strong acid as the catalyst, such as sulfuric acid, phosphoric acid, p-toluenesulfonic acid, methanesulfonic acid, oxalic acid, or the like.

(E-3) The above dicarboxylates (Ic') may also be formed through the steps of first reacting the acetylene alcohol corresponding to the unsaturated carbonyl compound or the precursor thereof of formula (IV) with the carboxylic acid corresponding to the aforesaid anhydride of formula (VIc) to form the mono-ester of said acid, and then further reacting the same with the carboxylic acid in the presence of a suitable rearrangement catalyst such as silver acetate or carbonate.

[I-3] Preferred examples of allylacetals (Ia), (Ib), and (Ic):

1. As the allylacetals to be employed as the starting material for the invention, the following are preferred, referring to the foregoing formulae (I), (Ia), (Ib), or (Ic).

In the allylacetals, $R_1$ and $R_2$ may be the same or different, each denoting a hydrogen atom or a hydrocarbon residue of 1 to 45 carbon atoms, preferably 1 to 20 carbon atoms, said $R_1$ and $R_2$ optionally forming an aliphatic or aromatic ring either independently of each other or as bonded together. Preferred examples of the aliphatic or aromatic ring are those three-membered or twelve-membered rings, particularly cyclopropane, cyclopentane, cyclohexane, benzene, naphthalene, cyclo-octane, and cyclododecane rings.

What is important for $R_1$ and $R_2$ is that, when they are other than hydrogen atoms, they should be bonded through carbon atoms with the carbon atom at the α-position.

Incidentally, the above aliphatic or aromatic ring may contain a hetero atom such as oxygen atom, which is inert to the reaction of the present invention.

The significance of the group $R_3$ to the invention is great. $R_3$ must not be a hydrogen atom.

As $R_3$, saturated or unsaturated aliphatic, alicyclic, or aromatic hydrocarbon residues of 1 to 40 carbons, particularly 1 to 10 carbons, are preferred. Especially, alkyl groups of 1 to 4 carbons are preferred as $R_3$, the most preferred being a methyl group.

$R_1$, $R_5$, $R_6$ and $R_7$ may be the same or different, and are preferably each selected from the group consisting of hydrogen atom and hydrocarbon residues of 1 to 10 carbons, particularly 1 to 4 carbons.

$R_8$ is either a hydrogen atom or a group selected from hydrocarbon residues of 1 to 45 carbons. $R_4$ may form an alicyclic ring together with $R_7$ or $R_6$. Similarly, $R_7$ may form an alicyclic ring together with $R_6$ or $R_8$. Alternatively, they may form a heterocyclic ring through an inert hetero atom such as oxygen atom. Again, $R_4$, $R_5$, $R_6$, $R_7$, and $R_8$ can each independently contain an alicyclic ring, an aromatic ring, or a heterocyclic ring.

Suitable $R_8$ is selected from the same group of members already described as to $R_1$ and $R_2$ while obviously $R_8$ may be the same as, or different from, $R_1$ and $R_2$.

A and B preferably are bonded together to form a double bond between the carbon atoms at the α- and β-positions in formula (I). On the other hand, they may be such groups which are eliminated during the heating of specified allylacetal derivatives of formula (I), (Ia), (Ib), or (Ic) to form the unsaturated carbonyl compounds of formula (II), and can form a double bond between the carbon atoms at the α- and β-positions as aforesaid. Preferred examples of such groups include alkoxy or carboxylic acid residue (acyl) groups as A, and hyrogen atom as B. Particularly alkoxy groups or carboxylic acid residues of 1 to 20 carbons are preferred as A.

$R_9$ in formula (V) denoting allyl alcohols useful for the preparation of allylacetal (I), (Ia), (Ib), or (Ic) is preferably a hydrogen atom, while it may be selected from the group consisting of carboxylic acid residues (acyl groups) of 1 to 10 carbons, particularly 1 to 5 carbons.

$R_{11}$ in formula (Ib) is preferably selected from the group consisting of hydrogen and hydrocarbon residues of 1 to 20 carbons, particularly 1 to 5 carbons, with methyl and ethyl groups being the most preferred.

$R_{12}$ in formula (Ic) is preferably selected from the group consisting of carboxylic acid residues (acyl groups) of 1 to 20 carbons, particularly 1 to 5 carbons, an acetyl group being the most preferred.

2. Specific examples of preferred diallylacetal (Ia) will be shown hereinbelow, by dividing the formula (Ia) into two parts (J) and (K) as shown below:

$$R_1-CH-\underset{A}{\underset{|}{C}}-CH-\underset{B}{\underset{|}{C}}-H \quad (J)$$
(with $R_2$, $R_3$ substituents)

and $$-\underset{R_5}{\underset{|}{C}}-\underset{R_6}{\underset{|}{C}}=C\underset{R_8}{\overset{R_7}{\diagdown}} \quad (K)$$

Examples of J (J-1) $CH_3-\underset{CH_3}{\underset{|}{C}}=CH-CH\diagdown$ (J-2) $CH_3-\underset{C_2H_5}{\underset{|}{C}}=CH-CH\diagdown$ (J-3) $CH_3-\underset{\underset{OCH_3}{|}}{\underset{|}{C}}-CH_2-CH\diagdown$
with CH_3

(J-4) $CH_3-CH-\underset{\underset{OCH_3}{|}}{\underset{|}{CH}}-CH\diagdown$
with CH_3

(J-5) $ClCH_2-\underset{CH_3}{\underset{|}{C}}=C-CH\diagdown$ (J-6) $C_2H_5-\underset{C_2H_5}{\underset{|}{C}}=C-CH\diagdown$ (J-7) $CH_3-\underset{\underset{OC_2H_5}{|}}{\underset{|}{C}}-CH_2-CH\diagdown$
with CH_3

Examples of K (i) K belonging to (Ia)

(K-1) $-CH_2-CH=CH_2$ (K-2) $-CH_2-CH=CH-CH_3$ (K-3) $-CH_2-CH=\underset{CH_3}{\underset{|}{C}}-CH_3$ (K-4) $-(-CH_2-CH=\underset{CH_3}{\underset{|}{C}}-CH_2-)_N-H$ (N = 2 – 10)

(K-5) $-CH_2-CH=\underset{CH_3}{\underset{|}{C}}-CH_2-(CH_2-CH_2-\underset{CH_3}{\underset{|}{CH}}-CH_2-)_n-H$ (n = 1 – 10)

(K-6) $(CH_2-CH=\underset{CH_3}{\underset{|}{C}}-CH_2-)_n CH_2-$ [2,2,6-trimethylcyclohexyl group]

(K-7) $-CH_2-$ [2,2,6-trimethylcyclohexenyl group]

(K-8) $-CH_2-\underset{CH_3}{\underset{|}{C}}=\underset{CH_3}{\underset{|}{C}}-CH=CH-$ [2,2,6-trimethylcyclohexyl]

(K-9) $-CH-(CH=\underset{CH_3}{\underset{|}{C}}-CH=CH-)_n$ [2,2,6-trimethylcyclohexyl] (n=1–10)

(K-10) $-CH_2-$ (furyl group)

(K-11) $-CH_2-$ (dihydrofuryl group)

(K-12) $-CH_2-CH=\underset{CH_3}{\underset{|}{C}}-CH_2-CH_3$ (K-13) $-CH_2-\underset{\underset{CH_3}{|}}{\underset{|}{C}}=CH_2$
with CH_3

(K-14) $-CH_2-\underset{CH_3}{\underset{|}{C}}=CH-CH_3$ (ii) K belonging to (Ib)

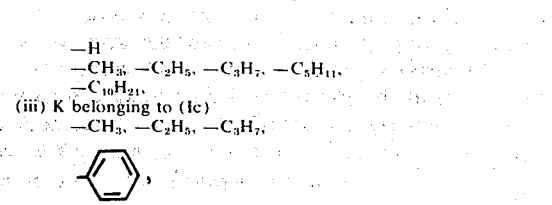

—H
—CH₃, —C₂H₅, —C₃H₇, —C₅H₁₁,
—C₁₀H₂₁,
(iii) K belonging to (Ic)
—CH₃, —C₂H₅, —C₃H₇,

[II] Preparation of dienyl ethers (III) or unsaturated carbonyl compounds (II). from allylacetal (Ia), (Ib), or (Ic):

The allyl acetals (Ia), (Ib), and (Ic) formed through the various methods described in (A), (B-1), (B-2), (C), (D), (E-1), (E-2), and (E-3), under the foregoing item [I-2], can be used for the preparation of dienyl ethers (III) or unsaturated carbonyl compounds (II), either as formed or after having been isolated from the reaction mixtures.

[II-1] Preparation of dienyl ethers (III) from allylacetal (Ia), (Ib), or (Ic):

Maintaining allylacetal derivatives (Ia), (Ib), or (Ic) in the presence of an acid catalyst in an inert organic solvent at a temperature ranging from normal to 150°C., preferably from normal to 130°C., the dienyl ethers of formula (III) are formed.

As the acid catalyst, organic or inorganic acid or the ammonium salt thereof, such as ammonium sulfate, ammonium nitrate, p-toluenesulfonic acid, the ammonium salt thereof, oxalic acid, the ammonium salt thereof, boric acid, and the like, can be used with advantage.

Examples of suitable inert organic solvents include the following:

i. aliphatic hydrocarbons, such as propane, butane, pentane, hexane, heptane, and octane;

ii. alicyclic hydrocarbons, such as cyclohexane, methylcyclohexane, ethylcyclohexane, decaline, etc.

iii. aromatic hydrocarbons, such as benzene, toluene, xylene (ortho-, meta-, para-), cumene, tetraline, etc.

iv. halogenated hydrocarbons, such as carbon tetrachloride, methylene chloride, chloroform, dichloroethane, trichloroethane, tetrachlorethane, chlorobenzene, dichlorobenzene, etc.

v. ethers such as diethyl ether, tetrahydrofuran, dioxane, etc. and vi. esters such as ethyl acetate, butyl acetate, methyl benzoate, dimethyl phthalate, diethyl phthalate, dibutyl phthalate, etc.

Among the foregoing solvents, aliphatic hydrocarbons (i) of 1 to 20 carbons, and aromatic hydrocarbons (iii) of 1 to 20 carbons are particularly preferred.

The above reaction for forming the dienyl ethers (III) is conveniently performed a a reduced pressure, while distilling the freed alcohols off from the reaction system. The reaction is normally completed within several minutes to 10 hours, ordinarily within approximately 1 to 4 hours.

Upon the completion of the reaction, the dienyl ethers (III) can be isolated by, for example, distilling the reaction liquid at a reduced pressure. [II-2] Preparation of unsaturated carbonyl compounds (II) from allylacetal (Ia), (Ib), or (Ic):

The unsaturated carbonyl compounds of formula (II) can be formed through a single-stage reaction, by heating the allylacetals of formula (Ia), (Ib), or (Ic) in an inert organic solvent, in the optional presence of a catalyst, at 50°–500°C.

As the heating temperatures, the range of 100 to 400°C. is more advantageously employed, particularly 130° to 400°C., more particularly 150° to 350°C., being employed with favorable results.

The presence of a catalyst is not essential, but preferably an acid catalyst, such as inorganic acid, organic acid, solid acid, and strong acid salt of weakly basic substance, can be used.

Specific examples of such acid catalysts include inorganic acids such as hydrochloric acid, sulfuric acid perchloric acid, phosphoric acid, boric acid, titanic acid, hypophosphorous acid, and metaboric acid. Also examples of organic acid catalysts include aliphatic carboxylic acids such as formic, acetic, propionic, butyric, monochloroacetic, dichloroacetic, trichloroacetic, stearic, palmitic, acrylic, oxalic, tartaric, and maleic acids; alicyclic carboxylic acids such as hexahydrobenzoic acid and naphthalenic acid; aromatic carboxylic acids such as benzoic, o-, m-, and p-toluic, phthalic, isophthalic, terephthalic, trimellitic, α- and β-naphthoic, anisic, chlorobenzoic, nitrobenzoic, cyanobenzoic, and bromobenzoic acids; aliphatic, alicyclic, or aromatic sulfonic acids such as methanesulfonic, ethanesulfonic, cyclohexanesulfonic, benzenesulfonic, and p-toluenesulfonic acids; and phosphinic or phosphonic acids such as methylphosphinic, ethylphosphinic, phenylphosphinic, methylphosphonic, ethylphosphonic, and benzylphosphonic acids. As the solid acid catalyst, in addition to the oxide type solid acids such as silica gel, silica-alumina, alumina, titanium oxide, germanium oxide, and boron oxide, those carried on salt or acid, such as NH₄Cl- carried silica-alumina, and zinc chloride-carried silica-alumina, can be named. Furthermore, examples of strong acid salts of weakly basic substances include ammonium chloride, ammonium nitrate, ammonium sulfate, ammonium phosphate, ferric chloride, zinc chloride, aluminium chloride, calcium chloride, tin chloride, ammonium p-toluene-sulfonate, and triethylammonium p-toluene-sulfonate. The foregoing are only given as examples, and it should be obvious that the scope of this invention is by no means thereby limited.

The acid catalyst employed in the subject process preferably has an acid strength (pKa) within the range of 0 to 10, particularly from 0 to 7, more particularly from 0 to 5.

The suitable amount of the acid catalyst is no more than 500 mol % per mol of allylacetals (I), preferably no more than 250 mol %, more preferably no more than 100 mol %. The lower limit is no less than $1 \times 10^{-6}$ mol %, preferably no less than $1 \times 10^{-5}$ mol %.

Also as the inert organic solvent, any of those listed as the solvent useful in the preparation of dienyl ethers (III) from allylacetal (Ia), (Ib), or (Ic), under the item [II-1], may be employed.

We have confirmed that during the above-described reaction, allylacetal (Ia), (Ib), or (Ic) is first converted to dienyl ethers (III), and then to unsaturated carbonyl compounds (II). However, the formation of said unsaturated carbonyl compounds (II) via dienyl ethers (III) rapidly progresses at the optimum temperature of the above specified temperature range, and consequently it is also possible to directly form unsaturated carbonyl compounds (II) from allylacetal (Ia), (Ib), or (Ic), through a single-stage reaction with high conversion and selectivity.

[III] Preparation of unsaturated carbonyl compounds (II) from dienyl ethers (III):

Dienyl ethers (III) formed from allylacetals (Ia), (Ib), or (Ic) by the process described in item [II-1] can be heated, either in the form of the reaction mixture as formed, or as isolated therefrom, under the conditions similar to those for the single-stage conversion of allylacetal (Ia), (Ib), or (Ic), to unsaturated carbonyl compounds (II) described in [II-2], to be converted to the object unsaturated carbonyl compounds.

The above-mentioned formation reaction of unsaturated carbonyl compounds (II) from dienyl ethers (III) proceeds smoothly even in the absence of a catalyst, but acid catalysts similar to those specified in item [II-2] can also be used, and again similar inert organic solvents specified in item [II-2] can be employed.

According to the invention, therefore, starting dienyl ethers (III) are not necessarily formed from allylacetal (Ia), (Ib), or (Ic), but dienyl ethers covered by formula (III) are usable regardless of the method of their preparation.

As has been explained so far, according to the invention, the unsaturated carbonyl compounds of formula (II),

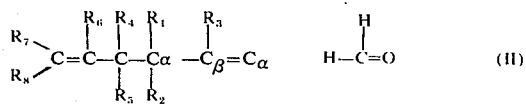

in which
R$_1$, R$_2$, R$_3$, R$_4$, R$_5$, R$_6$, R$_7$ and R$_8$, have the same definitions given in the early part of this specification, can be prepared from allylacetals of formula (I),

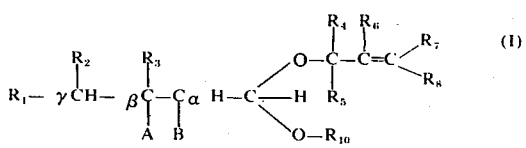

in which
R$_1$, R$_2$, R$_3$, R$_4$, R$_5$, R$_6$, R$_7$, R$_8$, R$_{10}$, A, and B have the already given definitions,
or of the previously given formula (Ia), (Ib), or (Ic), or from the dienyl ethers of formula (III),

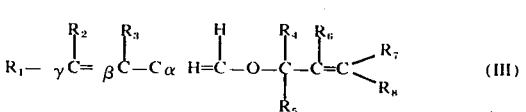

in which
R$_1$, R$_2$, R$_3$, R$_4$, R$_5$, R$_6$, R$_7$ and R$_8$, have the already given definitions, with high conversion and selectivity.

The process of this invention is unique in that the allylacetals have the construction as shown by formula (I), i.e., a hydrogen atom is bonded with the carbon atom at the α-position which is bonded with the carbonyl group

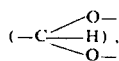

and the carbon atom at the β-position is bonded with an organic group, preferably a hydrogen residue (R$_3$) of 1 to 40 carbons, preferably of 1 to 10 carbons, said carbon atom at the β-position being bonded with no hydrogen. Similarly, the dienyl ether are characterized by their structure as illustrated by formula (III), in which the carbon atom at the α-position bonding with the carbonyl group

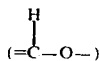

is bonded with a hydrogen atom, and the carbon atom at the β-position is bonded with an organic group (R$_3$) but not with a hydrogen atom. According to the invention, from allylacetals (I) or dienyl ethers (III) of such structures, unsaturated carbonyl compounds (II) in which the allyl group

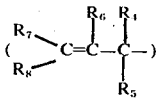

is introduced to the carbon atom located at the α-position to the carbonyl group are formed.

Such a reaction occurring according to the invention has never been disclosed in known literature.

As aforesaid, in the reaction to form unsaturated carbonyl compounds (II) from allylacetals (I), the allyl group

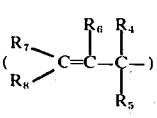

is introduced to the carbon atom located at the α-position to the carbonyl group

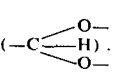

Consequently, if the two groups below bonding with the carbon atom at the β-position shown by formula (I), i.e.,
R$_3$—,
and

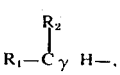

are organic groups differing from each other, for example, hydrocarbon residues, they each contain a carbon atom to be bonded with the carbon at the β-position, of formula (I), at different β-positions. Therefore, upon reaction, unsaturated carbonyl compound (II') in which the allyl group

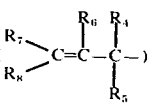

is bonded with the γ-positioned carbon atom in group $R_3$, and also unsaturated carbonyl compound (II) in which the allyl group is bonded with the γ-positioned carbon atom in the group

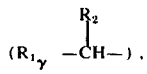

are formed.

Hereinafter the invention will be more specifically explained with reference to the following working Examples, with the understanding that the scope of this invention is in no way thereby limited.

Of the analyses data given in the Examples, the infrared absorption spectrum was measured with a Shimazu IR-27-G diffraction grating type device, using KBr plate as the cell. Also the NMR data were obtained by testing with a Nippon Denshi GNM-MH-100 (100 MHz), using $CCl_4$ as solvent.

The molecular weights and elementary analysis values were determined by high resolving power mass spectrum measured with a Nippon Denshi JMS-D-100 Model mass spectrometer. The quantitative analysis of the reaction results was performed by means of gas chromatography. The instrument employed was a Yanagimoto G-80 Model gas chromatogram, the column being mainly the 2-m glass column packed with OV-17-0.5 % glass beads carrier.

EXAMPLE 1

158 Parts of β-methyl-crotonaldehyde diethylacetal, 250 parts of prenol and 5 parts of ammonium nitrate were charged into a three-neck flask, and stirred for 4 hours at room temperature in a nitrogen atmosphere. Thereafter the inside pressure was reduced with an aspirator, and the stirring was continued for further approximately 8 hours at room temperature, while collecting the ethyl alcohol distilled off with the trap cooled with a dry ice-methanol system. Thus approximately 75 ml of ethyl alcohol was trapped. Adding 8 parts of sodium carbonate to the reaction product and vacuum-distilling the mixture, the following fraction of distillate was obtained:

boiling point:
70° – 120°C./0.7 mm Hg 160 parts.

Further subjecting the distillate to a fractionation distillation, the following results were obtained.

|  | boiling point |  |
|---|---|---|
| First fraction | ~40°C./0.9 mmHg | 22.1 parts |
| Second fraction | 55–58°C./0.9 mmHg | 10.6 parts |
| Third fraction | 58–60°C./0.9 mmHg | 37.1 parts |
| Fourth fraction | 92°C./0.9 mmHg | 89.2 parts |

Upon subjecting the distillate to gas chromatography, infrared and NMR analyses, the third fraction of the distillate was identified to be β-methyl-crotonaldehyde ethylprenylacetal [1-ethoxy-1-(3-methyl-2-butenyloxy)-3-methyl-2-butene], and the fourth fraction, to be β-methylcrotonaldehyde diprenylacetal [1,1-(3-methyl-2-butenyloxy)-3-methyl-2-butene]. The analyses results were as shown in Tables 9 and 10.

EXAMPLE 2

A three neck flask equipped with a rectification column was charged with 47 parts of prenyl alcohol, 12 parts of β-methyl-crotonaldehyde, and 200 parts of n-heptane. The system was heated to boiling in a nitrogen gas current, under normal pressure. The water formed was brought to azeotropy with n-heptane. Thus the water was separated, and the remaining n-heptane was recycled into the reaction system.

After 15 hours' heating, n-heptane was distilled off under normal pressure, and the residue was subjected to vacuum distillation.

Results of distillation

|  | boiling point |  |
|---|---|---|
| First fraction | 40–48°C./1 mmHg | 28.5 parts |
| Second fraction | 48–62°C./1 mmHg | 1 part |
| Third fraction | 65–75°C./1 mmHg | 1 part |
| Fourth fraction | 78–103°C./1 mmHg | 7.2 parts |

Upon gas chromatography analysis, the first fraction of distillate was found to be consisting of unreacted prenol and β-methyl-crotonaldehyde. The second and third fractions contained, respectively, 47 % and 73% of citral. Re-distilling the third fraction, a distillate boiling at 60° – 65°C. (authoritative boiling point of citral: 62°C./1 mmHg) was obtained, of which IR and NMR analyses results well corresponded with those of authentic sample.

Re-distilling the fourth fraction, the main distillate obtained boiled at 96° – 97°C./0.9 mmHg. The IR, NMR, and gas chromatography analyses results of the distillate coincided with those of β-methyl-crotonaldehyde-diphenylacetal which was synthesized through an alcohol exchange reaction between β-methyl-crotonaldehyde diethylacetal and prenyl alcohol.

EXAMPLES 3 – 20

The β-methyl-crotonaldehyde diprenylacetal [1,1-di-(3-methyl-2-butenyloxy)-3-methyl-2-butene] which was synthesized in the foregoing Example 1 or 2 was reacted in a sealed tube under various conditions. The results are shown in Tables 1, 2 and 3.

Table 1

| | Reaction condition | | | | | Result | |
|---|---|---|---|---|---|---|---|
| No. | Acetal or dienyl ether (part) | Catalyst (mol %) | Solvent (part) | Temperature (°C) | Time (min) | Conversion | Carbonyl compound obtained Selectivity |
| 3 | 2-[I] 0.1 | benzoic acid 0.5 | benzene 1.74 | 130 | 120 | 91.7 | 2-[III] 62.1 |
| 4 | 2-[I] 0.1 | benzoic acid 0.5 | benzene 1.74 | 250 | 5 | 100 | 2-[III] 97.1 |
| 5 | 2-[I] 0.1 | benzoic acid 0.5 | benzene 1.74 | 300 | 3 | 100 | 2-[III] 68.1 |

Table 2

| No. | Acetal or dienyl ether part | Catalyst (mol %) | Solvent (part) | Temperature (°C) | Time (min) | Conversion | Carbonyl compound obtained Selectivity |
|---|---|---|---|---|---|---|---|
| 6 | 2-[I] 0.1 | — | n-heptane 1.36 | 200 | 60 | 100 | 2-[III] 7.21 |
| 7 | 2-[I] 0.1 | — | chlorobenzene 2.20 | 150 | 300 | 100 | 2-[III] 78.1 |
| 8 | 2-[I] 0.1 | benzoic acid 0.5 | chlorobenzene 2.20 | 200 | 5 | 69.0 | 2-[III] 91.6 |
| 9 | 2-[I] 0.1 | benzoic acid 0.5 | ethyl acetate 1.79 | 250 | 5 | 89.9 | 2-[III] 93.5 |
| 10 | 2-[I] 0.1 | benzoic acid 0.5 | tetrahydrofurane 2.80 | 250 | 5 | 77.2 | 2-[III] 87.2 |
| 11 | 2-[I] 0.1 | benzoic acid 0.5 | cyclohexane 1.56 | 200 | 10 | 94.1 | 2-[III] 96.3 |
| 12 | 2-[I] 0.1 | benzoic acid 0.5 | — | 230 | 5 | 97.2 | 2-[III] 74.2 |

Table 3

| No. | Acetal or dienyl ether (part) | Catalyst (mol %) | Solvent (part) | Temperature (°C) | Time (min) | Conversion | Carbonyl compound obtained Selectivity |
|---|---|---|---|---|---|---|---|
| 13 | 2-[I] 0.1 | iso phthalic acid 0.5 | benzene 1.74 | 150 | 120 | 98.1 | 2-[II] 82.0 |
| 14 | 2-[I] 0.1 | o-nitro benzoic acid 0.5 | benzene 1.74 | 150 | 120 | 99.7 | 2-[II] 9.17 |
| 15 | 2-[I] 0.1 | oxalic acid 0.5 | benzene 1.74 | 150 | 120 | 100 | 2-[II] 91.9 |
| 16 | 2-[I] 0.1 | ammonium nitrate 0.5 | benzene 1.74 | 150 | 120 | 100 | 2-[II] 84.4 |
| 17 | 2-[I] 0.1 | ammonium sulfate 0.5 | benzene 1.74 | 150 | 120 | 100 | 2-[II] 79.2 |
| 18 | 2-[I] 0.1 | ammonium chloride 0.5 | benzene 1.74 | 150 | 120 | 79.7 | 2-[II] 67.5 |
| 19 | 2-[I] 0.1 | metane sulfonic acid 0.005 | benzene 1.74 | 200 | 10 | 96.5 | 2-[II] 95.9 |
| 20 | 2-[I] 0.1 | p-toluene sulfonic acid 0.005 | benzene 1.74 | 200 | 10 | 100 | 2-[II] 94.7 |

EXAMPLE 21

20 Parts of 1,1-di-(3-methyl-2-butenyloxy)-3-methyl-2-butene which was synthesized in Example 1, 43 parts of xylene, and 0.1 part of ammonium nitrate were charged in a flask, and the xylene was distilled off under reduced pressure (20 mmHg). Thereafter the bath temperature was maintained at not higher than 100°C., and the distillate was collected until the reaction was completed. Re-distilling the so obtained distillate, 5.15 parts of a fraction of a distillate boiling at 46.5°C./0.1 mmHg was obtained, which was confirmed to be 1-(3-methyl-2-butenyloxy)-3-methyl-1,3-butadiene from the results of IR, NMR, and high resolving power mass spectrum analyses. The analyses data are shown in Table 9.

EXAMPLE 22

25 Parts of β-methyl-crotonaldehyde diethylacetal, 50 parts of methallyl alcohol, and 0.5 part of ammonium nitrate were stirred together for 8 hours in a nitrogen gas current at room temperature and normal pressure. The ethanol formed at room temperature under reduced pressure was removed from the system during the subsequent 16 hours. To the reaction product, 1 part of sodium carbonate was added, and the product was distilled. 12.8 parts of the distillate boiling at 75° – 78°C./3 mmHg were confirmed to be β-methylcrotonaldehyde dimethallylacetal [1,1-di-(2-methyl-2-propenyloxy)-3-methyl-2-butene], from the results of IR and NMR analyses.

Also as the fraction of distillate recovered preceding the aboveidentified compound, 0.5 part of that boiling at 38°C./2 mmHg was obtained, which was confirmed to be 3-methylbutadiene-methallylether [1-(2-methyl-2-propenyloxy)-3-methyl-1,3-butadiene] from the results of IR and NMR analyses. The analyses results are shown in Table 19.

EXAMPLE 23

0.275 Part of the β-methylbutadiene-methallyl ether isolated in Example 22, and 5.2 parts of toluene were charged in a sealed tube, and after substituting the inside air with nitrogen, the tube was melt-sealed. After 2 hours' reaction at 220°C., the reaction product in the tube was analyzed by gas chromatography. It was thus discovered that the peak of the starting dienyl ether had disappeared, and a new peak was formed. The under various conditions, with the results being given in Tables 4 and 5, in which the marks of the fed starting materials and of the products correspond to the compounds of same marks shown in Tables 9 and 12.

Table 4

| No. | Acetal or dienyl ether (part) | Catalyst (mol %) | Solvent (part) | Temperature (°C) | Time (min) | Conversion | Carbonyl compound obtained Selectivity |
|---|---|---|---|---|---|---|---|
| 24 | 2-[III] 0.05 | — | benzene 0.87 | 50 | 120 | 4.1 | 2-[II] 35.9 |
| 25 | 2-[III] 0.05 | — | benzene 0.87 | 100 | 120 | 35.6 | 2-[II] 18.0 |
| 26 | 2-[III] 0.05 | — | benzene 0.87 | 150 | 5 | 37.1 | 2-[II] 24.6 |
| 27 | 2-[III] 0.05 | — | benzene 0.87 | 200 | 5 | 100 | 2-[II] 96.6 |
| 28 | 2-[III] 0.05 | — | benzene 0.87 | 300 | 5 | 100 | 2-[II] 80.8 |

Table 5

| No. | Acetal or dienyl ether (part) | Catalyst (mol %) | Solvent (part) | Temperature (°C) | Time (min) | Conversion | Carbonyl compound obtained Selectivity |
|---|---|---|---|---|---|---|---|
| 29 | 2-[III] 0.041 | — | n-heptane 0.68 | 180 | 120 | 100 | 2-[III] 90.2 |
| 30 | 2-[III] 0.05 | — | toluene 0.86 | 250 | 5 | 100 | 2-[III] 71.8 |
| 31 | 2-[III] 0.05 | — | diphenyl ether 1.15 | 250 | 5 | 100 | 2-[III] 83.6 |
| 32 | 2-[III] 0.05 | — | dibuthyl phthalate 1.05 | 250 | 5 | 100 | 2-[III] 53.5 |
| 33 | 5-[III] 0.05 | — | chloro benzene 1.10 | 250 | 5 | 100 | 5-[II] 80.1 |
| 34 | 5-[III] 0.05 | — | benzene 0.87 | 260 | 5 | 98.0 | 5-[II] 93.1 | yield after distilling the toluene off was 0.218 part. Upon analyzing the product by means of IR and NMR spectra, it was identified to be 1-formyl-2,5-dimethyl-1,5-hexadiene (3,6-dimethyl-2,6-heptadienal). The analyses results are given in Table 19.

EXAMPLE 24 – 34

The 1-(3-methyl-2-butenyloxy)-3-methyl-1,3-butadiene synthesized in Example 21 and 1-(3,7-dimethyl-2,6-octadienyloxy)-3-methyl-1,3-butadiene synthesized from 1,1-di(3,7-dimethyl-2,6-octadienyloxy)-3-methyl-2-butene-(3-methyl-2-butenal-digeranylacetal) similarly to Example 21 were reacted in a sealed tube

EXAMPLE 35 - 50

Various acetals and dienyl ethers synthesized in a manner similar to Example 1 and Example 2 and 21 were reacted in sealed tubes under various conditions, with the results shown in Tables 6 and 7. Also the structures, boiling points, and IR, NMR, and high resolving power mass spectra analyses results, of those acetals, dienyl ethers, and the carbonyl compounds formed are shown in Tables 8 through 19. The marks assigned to the fed materials and products in Tables 6 and 7 denote the compounds of corresponding marks in Tables 8 through 19.

Table 6

| No. | Acetal or dienyl ether (part) | Catalyst (mol %) | Solvent (part) | Temperature (°C) | Time (min) | Conversion | Carbonyl compound obtained Selectivity |
|---|---|---|---|---|---|---|---|
| 35 | 1-[I] 0.1 | benzoic acid 0.5 | benzene 1.74 | 250 | 10 | 96.0 | 1-[II] ≈100 |
| 36 | 1-[III] 0.05 | — | benzene 0.87 | 250 | 5 | ≈100 | 1-[II] ≈100 |
| 37 | 2-[I] 0.1 | p-toluene sulfonic acid 0.005 | benzene 1.74 | 200 | 10 | ≈100 | 2-[II] 94.7 |
| 38 | 2-[III] 0.05 | — | benzene 0.87 | 250 | 5 | ≈100 | 2-[II] ≈100 |
| 39 | 3-[I] 0.1 | oxalic acid 0.6 | benzene 1.74 | 200 | 10 | 94.2 | 2-[II] 58.5 |
| 40 | 4-[I] 0.1 | methane sulfonic acid 0.01 | benzene 1.74 | 250 | 5 | 97.1 | 2-[II] 92.4 |

Table 6-continued

| No. | Acetal or dienyl ether (part) | Catalyst (mol %) | Solvent (part) | Temperature (°C) | Time (min) | Conversion | Carbonyl compound obtained Selectivity |
|---|---|---|---|---|---|---|---|
| 41 | 5-[I] 0.1 | oxalic acid 0.5 | benzene 1.74 | 200 | 10 | 100 | 5-[II] 91.3 |
| 42 | 5-[III] 0.05 | — | n-dodecane 0.75 | 250 | 5 | 97.2 | 5-[II] ≈100 |
| 43 | 6-[I] 0.1 | isophthalic acid 0.5 | benzene 1.74 | 250 | 5 | 96.3 | 6-[II] 58.6 |
| 44 | 7-[I] 0.1 | benzoic acid 0.5 | benzene 1.74 | 270 | 5 | ≈100 | 7-[II] 81.7 |

Table 7

| No. | Acetal or dienyl ether (part) | Catalyst (mol %) | Solvent (part) | Temperature (°C) | Time (min) | Conversion | Carbonyl compound obtained Selectivity |
|---|---|---|---|---|---|---|---|
| 45 | 7-[III] 0.05 | — | benzene 0.87 | 250 | 5 | 95.5 | 7-[II] 47.6 |
| 46 | 8-[I] 0.1 | benzoic acid 0.5 | benzene 1.74 | 250 | 10 | 97.6 | 8-[II] 68.1 |
| 47 | 10-[I] 0.1 | benzoic acid 0.5 | benzene 1.74 | 250 | 10 | 100 | 10-[II] 94.2 |
| 48 | 10-[III] 0.05 | — | benzene 0.87 | 250 | 5 | 100 | 10-[II] 48.7 |
| 49 | 11-[I] 0.05 | benzoic acid 10 | benzene 0.87 | 250 | 5 | 90.9 | 11-[II] 62.4 |
| 50 | 12-[I] 0.05 | oxalic acid 0.5 | benzene 0.87 | 250 | 10 | 99.6 | 12-[II] 82.1 |

Table 8

Run No. 1

| Structure | | B.P. °C/mmHg | High-mass data Calculated | High-mass data Found | Infrared spectrum (specific absorption) | | NMR spectrum (specific absorption) | | |
|---|---|---|---|---|---|---|---|---|---|
| acetal | | | | | | | | τ value | H No. |
| $CH_3$       (c) (d) (e)<br>          O—$CH_2$—CH=$CH_2$<br>$CH_3$—C=CH—CH(a)<br>  (b)<br>          O—$CH_2$—CH=$CH_2$<br>1,1-di(2-propenyloxy)-3-methyl-2-butene<br>$C_{11}H_{18}O_2$ | [I] | 63°/3 | $C_{11}H_{18}O_2$<br><br>182.1307 | $C_{11}H_{18}O_2$<br><br>182.1312 | νC=C<br><br>δCH<br><br>νC—O—C | 1675 cm⁻¹<br>1645<br>920<br>1035<br>1070<br>1136 | H(d)<br><br>H(a)(b)(e)<br><br>H(c) | 3.98–4.40<br>(m)<br>4.73–4.98<br>(m)<br>6.05(d) | 2<br><br>6<br><br>4 |
| diethyl ether<br>   CH₃<br>    \|<br>$CH_2$=C—CH=CH—O—$CH_2$—CH=$CH_2$<br> (c)  (b)  (a)      (d)<br>1-(2-propenyloxy)-3-methyl-1,3-butadiene<br>$C_8H_{12}O$ | [III] | 57°/18 | $C_8H_{12}O$<br><br>124.0889 | $C_8H_{12}O$<br><br>124.0896 | C=C—C=C<br>νC=C<br><br>δCH<br><br>νC—O—C | 1635<br>1605<br>920<br>870<br>1170 | H(a)<br>H(b)<br>H(c)<br>H(d) | 3.58(d)<br>4.43(d)<br>5.35(d)<br>5.76(d) | 1<br>1<br>2<br>2 |
| unsaturated carbonyl compound<br>              CH₃<br>               \|<br>$CH_2$=CH—$CH_2$—$CH_2$—C=CH—CHO<br> (d)    (c)          (b)  (a)<br>3-methyl-2,6-heptadienal<br>$C_8H_{12}O$ | [II] | 79°/13 | $C_8H_{12}O$<br><br>124.0887 | $C_8H_{12}O$<br><br>124.0834 | C=C—CHO<br>νC=O<br><br>νC=C<br><br>δCH | 1675<br>1640<br>913 | H(a)<br>H(b)(c)<br><br>H(d) | 0.25(d)<br>4.12–4.38<br>(m)<br>4.92–5.14<br>(m) | 1<br>2<br><br>2 |

Table 9

Run No. 2

| Structure | B.P. °C/mmHg | High-mass data Calculated | Found | Infrared spectrum (specific absorption) | | NMR spectrum (specific absorption) | | |
|---|---|---|---|---|---|---|---|---|
| | | | | | | | $\tau$ value | H number |
| acetyl | | | | | | | | |
| $CH_3-\underset{(b)}{C}=CH-CH\underset{(a)}{\overset{CH_3}{\underset{|}{\bigg\langle}}}\begin{array}{l}O-CH_2-CH=\underset{(d)}{C}-CH_3\\O-CH_2-CH=\underset{}{C}-CH_3\\\phantom{O-CH_2-CH=}CH_3\end{array}$ [I] | 92/0.9 | $C_{15}H_{26}O_2$ | $C_{15}H_{26}O_2$ | $\nu C=C$ | 1675 | | | |
| | | | | $\nu C-O-C$ | 1072, 1013 | H(b)(d) | 4.68–4.82(m) | 3 |
| 1,1-di(3-methyl-2butenyloxy)-3-methyl-2-butene $C_{15}H_{26}O_2$ | | 238.1932 | 238.1929 | | | H(a) | 4.95(d) | 1 |
| | | | | | | H(c) | 6.08(d) | 4 |
| diethyl ether | | $C_{10}H_{16}O$ | $C_{10}H_{16}O$ | $C=C-C=C$ | 1635 | H(a) | 3.68(d) | 1 |
| $CH_2=\underset{(c)}{\overset{CH_3}{\underset{|}{C}}}-CH=CH-O-CH_2-CH=\underset{(e)}{\overset{CH_3}{\underset{|}{C}}}-CH_3$ [III] | 46.5°/0.1 | | | $\nu C=C$ | 1605 | H(b) | 4.50(d) | 1 |
| | | | | $\delta CH$ | 865 | H(e) | 4.70(t) | 1 |
| 1-(3-methyl-2-butenyloxy)-3-methyl-1,3-butadiene $C_{10}H_{16}O$ | | 152.1201 | 152.1204 | $\nu C-O-C$ | 1160 | H(c) | 5.48(d) | 2 |
| | | | | | | H(d) | 5.83(d) | 2 |
| unsaturated carbonyl compound | | $C_{10}H_{16}O$ | $C_{10}H_{16}O$ | $C=C-CHO$ | | H(a) | 0.08–0.26(t) | 1 |
| $CH_3-\underset{(c)}{\overset{CH_3}{\underset{|}{C}}}=CH-CH_2-CH_2-\underset{(b)}{\overset{CH_3}{\underset{|}{C}}}=CH-CHO\underset{(a)}{}$ [II] | 117–9/20 | | | $\nu C=O$ | 1670 | H(b) | 4.26(d) | 1 |
| | | | | $C=C$ | | | | |
| 3,7-dimethyl-2,6-octadienal $C_{10}H_{16}O$ | | 152.1201 | 152.1182 | $\nu C=C$ | 1630 | H(c) | 4.84–5.04(m) | 1 |

Table 10

Run No. 3

| Structure | B.P. °C/mmHg | High-mass data Calculated | Found | Infrared spectrum (specific absorption) | | NMR spectrum (specific absorption) | | |
|---|---|---|---|---|---|---|---|---|
| | | | | | | | $\tau$ value | H number |
| acetal | | | | | | | | |
| $CH_3-\underset{(b)}{\overset{CH_3}{\underset{|}{C}}}=CH-CH\underset{(a)}{\overset{\phantom{X}}{\underset{}{\bigg\langle}}}\begin{array}{l}\underset{(c)}{OCH_2}-\underset{(d)}{CH}=\underset{}{\overset{CH_3}{\underset{|}{C}}}-CH_3\\OC_2H_5\end{array}$ [I] | 58–60/0.9 | $C_{12}H_{22}O_2$ | $C_{12}H_{22}O_2$ | $\nu C=C$ | 1675 | | | |
| | | | | $\nu C-O-C$ | 1137, 1088, 1074, 1041 | H(b)(d) | 4.68–4.82(m) | 2 |
| | | | | | | H(a) | 4.97(d) | 1 |
| 1-ethoxy-1-(3-methyl-2-butenyloxy)3-methyl-2-butene $C_{12}H_{22}O_2$ | | 198.1619 | 198.1599 | | | H(c) | 6.08(d) | 2 |
| dienyl ether | | | | $C=C-C=C$ | 1635 | H(a) | 3.68(d) | 1 |
| $CH_2=\overset{CH_3}{\underset{|}{C}}-CH=CH-O-CH_2-CH=\overset{CH_3}{\underset{|}{C}}-CH_3$ [III] | 46.5/0.1 | $C_{10}H_{16}O$ | $C_{10}H_{16}O$ | $\delta C=C$ | 1605 | H(b) | 4.50(d) | 1 |
| | | | | $\delta CH$ | 865 | H(e) | 4.70(t) | 1 |
| 1-(3-methyl-3-butenyloxy)-3-methyl-1,3-butadiene $C_{10}H_{16}O$ | | 152.1202 | 152.1204 | $\nu C-O-C$ | 1160 | H(c) | 5.48(d) | 2 |
| | | | | | | H(d) | 5.38(d) | 2 |
| unsaturated carbonyl compound | | $C_{10}H_{16}O$ | $C_{10}H_{16}O$ | $C=C-CHO$ | | H(a) | 0.08–0.26(t) | 1 |
| $CH_3-\overset{CH_3}{\underset{|}{C}}=CH-CH_2-CH_2-\overset{CH_3}{\underset{|}{C}}=CH-CHO$ [II] | 117–9/20 | | | $\nu C=O$ | 1670 | H(b) | 4.26 (d) | 1 |
| | | | | $C=C$ | 1630 | | 4.84– | |
| 3,7-dimethyl-2,6-octadienal $C_{10}H_{16}O$ | | 152.1201 | 152.1182 | $\nu C=C$ | | H(c) | 5.04(m) | 1 |

Table 11

Run No. 4

| Structure | B.P. °C/mmHg | High-mass data Calculated | Found | Infrared spectrum (specific absorption) | | NMR spectrum (specific absorption) | | |
|---|---|---|---|---|---|---|---|---|
| Acetal | | | | | | | τ value | H no. |
| $CH_3-\underset{\underset{O-C_2H_5}{|}}{\overset{\overset{CH_3}{|}}{C}}-CH_2-\underset{(a)}{CH}\diagdown \overset{OCH_2-\overset{(b)}{CH}=\overset{(c)}{\overset{\overset{CH_3}{|}}{C}}-CH_3}{OCH_2-CH=\underset{\underset{CH_3}{|}}{C}-CH_3} \text{ [I]}$ | 99–107/ 0.1 | $C_{17}H_{32}O_3$ 284.2352 | $C_{17}H_{32}O_3$ 284.2368 | $\nu C=C$ $\nu C-O-C$ | 1675 1110, 1070, 1042, 1022 | H(c) H(a) H(b) | 4.73(t) 5.39(t) 6.07(d) | 2 1 2 |
| 1,1-di(3-methyl-2-butenoxy)-3-ethoxy-3-methyl-butene $C_{17}H_{32}O$ | | | | | | | | |
| unsaturated carbonyl compound | | | | | | | | |
| $CH_3-\underset{(d)}{\overset{\overset{CH_3}{|}}{C}}=CH-CH_2-CH_2-\underset{(b)}{\overset{\overset{CH_3}{|}}{C}}=\underset{(a)}{CH}-CHO$ [II] 3,7-dimethyl-2,6-octadienal $C_{10}H_{16}O$ | 117–9/ 20 | $C_{10}H_{16}O$ 152.1201 | $C_{10}H_{16}O$ 152.1182 | $C=C-CHO$ $C=C$ $\nu C=C$ | 1670 1630 | H(a) H(b) H(c) | 0.08– 0.26(t) 4.26(d) 4.84– 5.04(m) | 1 1 1 |

Table 12

Run No. 5

| Structure | B.P. °C/mmHg | High-mass data Calculated | Found | Infrared spectrum (specific absorption) | | NMR spectrum (specific absorption) | | |
|---|---|---|---|---|---|---|---|---|
| acetyl | | | | | | | τ value | H no. |
| $CH_3-\underset{(b)}{\overset{\overset{CH_3}{|}}{C}}=CH-\underset{(a)}{CH}\diagdown\diagdown\overset{OCH_2-\overset{(c)}{CH}=\underset{\underset{CH_3}{|}}{\overset{(d)}{C}}-CH_2-CH_2-\overset{(e)}{CH}=\underset{\underset{CH_3}{|}}{\overset{\overset{CH_3}{|}}{C}}-CH_3}{OCH_2-CH=\underset{\underset{CH_3}{|}}{C}-CH_2-CH_2-CH=\underset{\underset{CH_3}{|}}{\overset{\overset{CH_3}{|}}{C}}-CH_3}$ [I] | 180/0.8 | $C_{25}H_{42}O_2$ 374.3187 | $C_{25}H_{42}O_2$ 374.3110 | $\nu C=C$ $\nu C-O-C$ | 1670 1015 1070 1095 1135 | H (a,b, d,e) H(c) | 4.65 –5.00 (m) 6.50 (d) | 6 4 |
| 1,1-di(3,7-dimethyl-2,6-octadienyloxy)-3-methyl-2-butene $C_{25}H_{42}O_2$ | | | | | | | | |
| dienyl ether | | | | | | | | |
| $\underset{(c)}{CH_2}=\underset{(b)}{\overset{\overset{CH_3}{|}}{C}}-\underset{(a)}{CH}=CH-O-\underset{(d)}{CH_2}-\underset{(e)}{CH}-CH=\underset{\underset{CH_3}{|}}{C}-CH_2-CH_2-\underset{(f)}{CH}=\overset{\overset{CH_3}{|}}{C}-CH_3$ [III] | 80–85°/ 0.08 | $C_{15}H_{24}O$ 220.1947 | $C_{15}H_{24}O$ 220.1888 | $C=C-C=C$ $\nu C=C$ $\delta CH$ $\nu C-O-C$ | 1635 1602 865 1170 | H(a) H(b) H(e) H(f) H(c) H(d) | 3.59 (d) 4.38 (d) 4.48 (m) 4.95 (m) 5.37 (d) 5.79 (d) | 1 1 1 1 2 2 |
| 1-(3,7-dimethyl-2,6-octadienyloxy)-3-methyl-1,3-butadiene $C_{15}H_{24}O$ | | | | | | | | |
| unsaturated carbonyl compound | | | | | | | | |
| $CH_3-\underset{(d)}{\overset{\overset{CH_3}{|}}{C}}=CH-CH_2-CH_2-\underset{(c)}{\overset{\overset{CH_3}{|}}{C}}=CH-CH_2-CH_2-\underset{(b)}{\overset{\overset{CH_3}{|}}{C}}=\underset{(a)}{CH}-CHO$ [II] 3,7,11-trimethyl-2,6,10-dotecatrienal $C_{15}H_{24}O$ | 172–4/ 14 | $C_{15}H_{24}O$ 220.1828 | $C_{15}H_{24}O$ 220.1820 | $C=C-CHO$ $\nu CO$ $C=C$ $\nu C=C$ | 1676 1628 | H(a) H(b) H (c,d) | 0.11 –0.26 (t) 4.25 (d) 4.84 –5.08 (m) | 1 1 2 |

Table 13

Run No. 6

| Structure | B.P. °C/mmHg | High-mass data Calculated | Found | Infrared spectrum (specific absorption) | NMR spectrum (specific absorption) τ value | H no. |
|---|---|---|---|---|---|---|
| acetal<br><br>$CH_3$<br>$CH_3\overset{\|}{C}=CH-CH(a)$<br>(b)<br>$\diagdown O-CH_2-CH=\overset{CH_3}{\underset{\|}{C}}-CH_2-CH_2-CH=\overset{CH_3}{\underset{\|}{C}}-CH_2-CH_2-CH=\overset{CH_3}{\underset{\|}{C}}-CH_3$<br>(c) (d) (e) (f)<br>$\diagdown O-CH_2-CH=\overset{\|}{C}-CH_2-CH_2-CH=\overset{\|}{C}-CH_2-CH_2-CH=\overset{\|}{C}-CH_3$<br>$\phantom{xxxxx}CH_3\phantom{xxxxxxx}CH_3\phantom{xxxxxxx}CH_3$<br><br>1,1-di(3,7,11-trimethyl-2,6,10-dodecatrienoxyl)-3-methyl-2-butene<br>$C_{35}H_{58}O_2$ | 234–240°/0.25<br><br>[I] | $C_{35}H_{58}O_2$<br><br><br><br>510.4440 | $C_{35}H_{58}O_2$<br><br><br><br>510.4411 | νC=C 1670<br><br>νC–O–C 1132<br>1100<br>1070<br>1012 | H(a,b) 4.66<br>H(d,e,f) -5.00 (m)<br>H(c) 6.07<br><br>(d) | 8<br><br>4 |
| unsaturated carbonyl compound<br>$CH_3\phantom{xx}CH_3\phantom{xx}CH_3\phantom{xx}CH_3$<br>$CH_3-\overset{\|}{C}=CH-CH_2-CH_2-\overset{\|}{C}=CH-CH_2-CH_2-\overset{\|}{C}=CH-CH_2-CH_2-\overset{\|}{C}=CH-CHO$<br>(b) (a)<br><br>3,7,11,15-tetramethyl-2,6,10,14-hexadecatetraenal<br>$C_{20}H_{32}O$ | [II]<br>155–156/3 | $C_{20}H_{32}O$<br><br>288.2456 | $C_{20}H_{32}O$<br><br>288.2524 | C–C–CHO<br>νC=O 1675<br>C=C<br>νC=C 1630 | H(a) 0.14<br>(d)<br>H(b) 4.24<br>(d) | 1<br><br>1 |

Table 14

Run No. 7

| Structure | B.P. °C/mmHg | High-mass data Calculated | Found | Infrared spectrum (specific absorption) | NMR spectrum (specific absorption) τ value | H number |
|---|---|---|---|---|---|---|
| acetyl<br>$CH_3\phantom{xxxx}$(c) $CH_3\ CH_3$<br>$CH_3-\overset{\|}{C}=CH-CH(a)\diagup\!\!\!\overset{O-CH_2}{\phantom{x}}\diagdown$<br>(b)$\phantom{xxxx}\diagdown O-CH_2\diagup\phantom{xx}CH_3$<br><br>1,1-di(β-cyclogelanyloxy)-3-methyl-2-butene $C_{25}H_{42}O_2$ | [I]<br>173–175<br>0.1 | $C_{25}H_{42}O_2$<br><br><br>374.3185 | $C_{25}H_{42}O_2$<br><br><br>374.3205 | νC=C 1680<br>1657<br>νC–O–C 1060<br>1040<br>1010 | H(a) 4.95(d)<br>H(b) 4.72(d)<br>H(c) 6.08(Q) | 1<br>1<br>4 |
| diethyl ether<br>$\phantom{xx}CH_3\phantom{xxxxxxxx}CH_3\ CH_3$<br>$CH_2=\overset{\|}{C}-CH=CH-O-CH_2-\diagup\!\!\!\phantom{xx}$<br>(c) (b) (a)$\phantom{xxxxxxx}CH_3$<br><br>1-(β-cyclogelanyloxy)-3-methyl-1,3-butadiene $\phantom{xx}C_{15}H_{24}O$ | [III]<br>78–83°<br>0.07 | $C_{15}H_{24}O$<br><br><br>220.1828 | $C_{15}H_{24}O$<br><br><br>220.1809 | C=C–C=C<br>νC=C 1605<br>1637<br>=CH δCH 865<br>C–O–C<br>νC–O–C 1165 | H(a) 3.51(d)<br>H(b) 4.45(d)<br>H(c) 5.36(d)<br>H(d) 5.85(s) | 1<br>1<br>2<br>2 |
| unsaturated carbonyl compound<br>$CH_3\ CH_3\phantom{xxxxx}CH_3$<br>$\diagup\!\!\!-CH_2-CH_2-\overset{\|}{C}=CH-CHO$<br>$\diagdown CH_3\phantom{xxxxxxx}$(b) (a)<br><br>β-dihydroionylidene acetoaldehyde $C_{15}H_{24}O$ | [II]<br>98°/0.1 | $C_{15}H_{24}O$<br><br>220.1829 | $C_{15}H_{24}O$<br><br>220.1855 | C=C–CHO<br>νC=O 1675<br>C=C<br>νC=C 1630 | H(a) 0.10(d)<br>H(b) 4.19(d) | 1<br>1 |

Table 15

Run No. 8

| Structure | B.P. °C/mmHg | High-mass data Calculated | Found | Infrared spectrum (specific absorption) | NMR spectrum (specific absorption) τ value | H no. |
|---|---|---|---|---|---|---|
| acetal<br>$\phantom{xxxx}CH_3\phantom{xx}$(c) (d) $CH_3$<br>$CH_3-CH_2-\overset{\|}{C}=CH-CH\diagup\!\!\!\overset{O-CH_2-CH=\overset{\|}{C}-CH_3}{\phantom{x}}$<br>(b) (a)$\diagdown\phantom{xx}\underset{CH_3}{\overset{\|}{\phantom{x}}}$<br>$\phantom{xxxxxxxx}\diagdown O-CH_2-CH=\overset{\|}{C}-CH_3$<br>$\phantom{xxxxxxxxxxxx}CH_3$<br><br>1,1-di(3-methyl-2-butenyloxy)-3-methyl-2-pentene<br>$C_{16}H_{28}O_2$ | [I]<br>100–104/0.15 | $C_{16}H_{28}O_2$<br><br><br>252.2052 | $C_{16}H_{28}O_2$<br><br><br>252.2067 | νC=C 1670<br>νC–O–C 1135<br>1115<br>1085<br>1010 | H(b)(d) 4.66<br>–4.83(m)<br>H(a) 4.93(d)<br>H(c) 6.07(d) | 3<br><br>1<br>4 |

Table 15-continued

Run No. 8

| Structure | B.P. °C/mmHg | High-mass data Calculated / Found | Infrared spectrum (specific absorption) | NMR spectrum (specific absorption) | |
|---|---|---|---|---|---|
| unsaturated carbonyl compound $CH_3-\underset{(c)}{C}(CH_3)=CH-CH_2-CH_2-\underset{(b)}{C}(CH_2-CH_3)=\underset{(a)}{CH}-CHO$ [II] 3-ethyl-7-methyl-2,6-octadienal $C_{11}H_{18}O$ | 88°/3.5 | $C_{11}H_{18}O$ / $C_{11}H_{18}O$ 166.1369 / 166.1373 | C=C—CHO $\nu$C=O 1670 C=C $\nu$C=C 1625 | H(a) 0.16(d) H(b) 4.29(d) H(c) 4.86 −5.02(m) | 1 1 1 |

Table 16

Run No. 9

| Structure | High-mass data Calculated / Found | Infrared spectrum (specific absorption) | NMR spectrum (specific absorption) | | |
|---|---|---|---|---|---|
| acetal $CH_3-\underset{(b)}{C}(CH_3)=CH-\underset{(a)}{CH}\begin{pmatrix} O-CH_2-CH=C(CH_3)-(CH_2-CH_2-C(CH_3))_3-CH_3 \\ O-CH_2-CH=C(CH_3)-(CH_2-CH_2-C(CH_3))_3-CH_3 \end{pmatrix}$ [I]' 1,1-di(3,7,11,15-tetramethyl-2-hexadecanoxyl)-3-methyl-2-butene $C_{45}H_{86}O_2$ | $C_{45}H_{86}O_2$ / $C_{45}H_{86}O_2$ 658.6445 / 658.6554 | $\nu$C=C 1670 $\nu$C—O—C 1140 1070 1018 | | $\tau$ value H(a) 4.95(d) H(b) 4.60− (d) 4.82(m) H(c) 6.08(d) | H no. 1 3 4 |
| unsaturated carbonyl compound $H(CH_2-CH(CH_3)-CH_2-CH_2)_3CH_2-\underset{(c)}{C}(CH_3)=CH-CH_2-CH_2-\underset{(b)}{C}(CH_3)=\underset{(a)}{CH}-CHO$ [II]$^{(2)}$ 3,7,11,15,19-pentamethyl-2,6-eicosadienal $C_{25}H_{46}O$ | $C_{25}H_{46}O$ / $C_{25}H_{46}O$ 362.3190 / 362.3222 | C=C—CHO $\nu$C=O 1677 $\nu$C=C 1631 | | H(a) 0.13 −0.28(t) H(b) 4.24(d) H(c) 4.91 −5.01(m) | 1 1 1 |

$^{(1)}$B.P. °C.mmHg — 225/0.004
$^{(2)}$B.P. °C/mmHg — 182–185/0.3

Table 17

Run No. 10

| Structure | B.P. °C/mmHg | High-mass data Calculated / Found | Infrared spectrum (specific absorption) | NMR spectrum (specific absorption) | |
|---|---|---|---|---|---|
| acetyl $CH_3-\underset{(b)}{C}(CH_3)=CH-\underset{(a)}{CH}\begin{pmatrix} O-CH_2-CH=C(CH_3)-CH_2-CH_3 \\ O-CH_2-CH=C(CH_3)-CH_2-CH_3 \end{pmatrix}$ [I] 1,1-di(3-methyl-2-pentenyloxy)-3-methyl-2-butene $C_{17}H_{30}O_2$ | 112–117/ 0.08 | $C_{17}H_{30}O_2$ / $C_{17}H_{30}O_2$ 266.2246 / 266.2233 | $\nu$C=C 1672 $\nu$C—O—C 1136 1118 1070 1015 | $\tau$ value H(b)(d) 4.68 −4.82(m) H(a) 4.95(d) H(c) 6.07(d) | H number 3 1 4 |
| dienyl ether $\underset{(c)}{CH}=\underset{(b)}{C}(CH_3)-\underset{(a)}{CH}=CH-O-CH_2-\underset{(d)}{CH}=C(CH_3)-CH_2-CH_3$ [III] 1-(3-methyl-2-pentenyloxy)-3-methyl-1,3-butadiene $C_{11}H_{18}O$ | 55–57/ 0.5 | $C_{11}H_{18}O$ / $C_{11}H_{18}O$ 166.1359 / 166.1395 | C=C—C=C $\nu$C=C C=C 1675 1635 —C=CH$_2$CH 920 $\nu$C—O—C 1170 | H(a) 3.55(d) H(b) 4.45(d) H(c) 5.35(d) H(d) 5.77(d) | 1 1 2 2 |
| unsaturated carbonyl compound $CH_3-CH_2-\underset{(c)}{C}(CH_3)=CH-CH_2-CH_2-\underset{(b)}{C}(CH_3)=\underset{(a)}{CH}-CHO$ [II] 3,7-dimethyl-2,6-nonadienal $C_{11}H_{18}O$ | 69–70/ 0.1 | $C_{11}H_{18}O$ / $C_{11}H_{18}O$ 166.1358 / 166.1352 | C=C—CHO $\nu$C=O 1675 C=C $\nu$C=C 1630 | H(a) 0.08 −0.24(m) H(b) 4.23(d) H(c) 4.82 −5.02(m) | 1 1 1 |

Table 18

| Run No. 11 Structure | B.P. °C/mmHg | High-mass data Calculated | Found | Infrared spectrum (specific absorption) | | NMR spectrum (specific absorption) | | |
|---|---|---|---|---|---|---|---|---|
| | | | | | | | $\tau$ value | H number |
| acetyl structure with H(d), H(e), CH$_3$, (c), O-CH$_2$, H(f), CH$_3$-C=CH-CH (a)(b), O-CH$_2$, H, H [I] 1,1-di-(2-furfuryloxy)-3-methyl-2-butene $C_{15}H_{18}O_4$ | 127/0.8 | $C_{15}H_{18}O_4$ 262.1206 | $C_{15}H_{18}O_4$ 262.1207 | $\nu$C=C $\nu$C—O—C | 1677 cm$^{-1}$ 1070 1008 1500 880 733 | H(f) H(e,d) H(a,b) H(c) | 2.75(s) 3.83(s) 4.78(s) 5.59(s) | 2 4 2 4 |
| unsaturated carbonyl compound (d)(c) H H CH$_3$ H CH$_2$—CH$_2$—C=CH—CHO [II] (e) (b)(a) 5-(2-furyl)-3-methyl-2-pentanal $C_{10}H_{12}O_2$ | 75°/ 0.25 | $C_{10}H_{12}O_2$ 164.0837 | $C_{10}H_{12}O_2$ 164.0830 | C=C—CHO $\nu$CO | 1672 1507 883 732 | H(a) H(e) H(d) H(c) H(b) | 0.11 −0.37(Q) 2.76(s) 3.81(d) 4.05(d) 4.23 | 1 1 1 1 1 |

Table 19

| Run No. 12 Structure | B.P. °C/mmHg | High-mass data Calculated | Found | Infrared spectrum (specific absorption) | | NMR spectrum (specific absorption) | | |
|---|---|---|---|---|---|---|---|---|
| | | | | | | | $\tau$ value | H number |
| acetyl (c) CH$_3$ CH$_3$ O—CH$_2$—C=CH$_2$ (d) H$_3$C—C=CH—CH (b)(a) O—CH$_2$—C=CH$_2$ CH$_3$ 1,1-di-(2-methyl-2-propenyloxy)-3-methyl-2-butene $C_{13}H_{22}O_2$ | [I] 75–78/3 | $C_{13}H_{22}O_2$ 210.1619 | $C_{13}H_{22}O_2$ 210.1603 | $\nu$C=C $-\overset{\|}{C}$=CH$_2\delta$CH $\nu$C—O—C | 1680 1660 895 1137 1080 1020 | H(b) H(a) H(d) H(c) | 4.73(d) 4.87(d) 5.14(d) 6.15(s) | 1 1 4 4 |
| diethyl ether CH$_3$ CH$_3$ CH$_2$=C—CH=CH—O—CH$_2$—C=CH$_2$ (c)(b)(a)(d)(e) 1-(2-methyl-2-propenyloxy)-3-methyl-1,3-butadiene $C_9H_{14}O$ | [III] 38/2 | $C_9H_{14}O$ 138.1045 | $C_9H_{14}O$ 138.1049 | C=C—C=C $\nu$C—C $-\overset{\|}{C}$=CH$_2\delta$CH $\nu$CH | 1650 1637 920 900 1160 | H(a) H(b) H(c) H(e) H(d) | 3.62(d) 4.44(d) 5.10(d) 5.37(d) 5.91(s) | 1 1 2 2 2 |
| unsaturated carbonyl compound CH$_3$ CH$_3$ CH$_2$=C—CH$_2$—CH$_2$—C=CH—CHO (c) (b)(a) 3,6-dimethyl-2,6-heptadienal $C_9H_{14}O$ | [II] 70/3.5 | $C_9H_{14}O$ 138.1044 | $C_9H_{14}O$ 138.1009 | C=C—CHO $\nu$C=O $-\overset{\|}{C}$=CH$_2\delta$CH | 1672 | H(a) H(b) H(c) | 0.09 −0.23(t) 4.22(d) 5.28(s) | 1 1 2 |

EXAMPLE 51

15.8 Parts of β-methyl-crotonaldehyde diethylacetal (1,1-diethoxy-3-methyl-2-butene), 21.5 parts of prenol (3-methyl-2-butenol), and 0.15 part of ammonium nitrate, were charged in a three neck flask. Similar to Example 1, the ethanol formed under reduced pressure was distilled off in a N$_2$ gas atmosphere at room temperature. After confirming by means of gas chromatography that all of the β-methyl-crotonaldehyde diethylacetal was converted, the reaction mixture as it was, i.e., without isolating and refining the reaction product, was thermally decomposed under the following conditions.

0.1 Part of the reaction product, 1.74 parts of benzene, and 0.0000037 part of methanesulfonic acid were charged into a sealed tube, and reacted at 250°C. for 5 minutes. The product was subjected to gas chromatography analysis. It was thus confirmed that citral (3,7-dimethyl-2,6-octadienal) was obtained at the selectivity of 80.8% to the originally fed β-methyl-croton aldehyde diethylacetal.

EXAMPLE 52

15.8 Parts of β-methyl-crotonaldehyde diethylacetal (1,1diethoxy-3-methyl-2-butene),88.8 parts of phytol and 0.2 part of ammonium nitrate, were charged into a three neck flask. Similar to Example 51, the ethanol formed under reduced pressure was distilled off. After confirming by means of gas chromatography that all of the β-methyl-crotonaldehyde diethylacetal was converted, the reaction mixture as it was, i.e., without isolating and refining the reaction product, was thermally decomposed under the following conditions.

0.1 Part of the reaction product, 1.74 parts of benzene, and 0.00018 part of benzoic acid were charged into a sealed tube, and reacted at 250°C. for 10 minutes. The product was subjected to gas chromatography analysis. It was thus confirmed that 3,7,11,15,19-pentamethyl-2,6-eicosadienal was obtained at the selectivity of 69.5% to the originally fed β-methyl-crotonaldehyde diethylacetal. The analytical value of the resulting acetal and aldehyde is shown in Table 16.

COMPARATIVE EXAMPLE 10 parts of crotonaldehyde dimethylacetal (1,1-di-(2-methylpropenyloxy)-2-butene) and 1 part of alumina were charged into a flask equipped with a distillation column and distilled slowly in a stream of $N_2$ gas at a bath temperature of 210°C. After re-distillation of the distillate, there was obtained 0.56 part of a distillate at 77°C/17 mmHg. abs.

From the result shown in Table 20, it was confirmed that said distillate was 3-formyl-5-methyl-2,5-hexadiene, but 6-methyl2,6-heptadienal to be prepared in the present invention could not be obtained by this method.

in which:

$R_1$ and $R_2$ are either the same or different, each being selected from the group consisting of hydrogen and hydrocarbon residues of 1 to 20 carbon atoms;

$R_3$ is selected from the group consisting of saturated and unsaturated aliphatic, alicyclic, and aromatic hydrocarbon residues of 1 to 10 carbon atoms;

$R_4$, $R_5$, $R_6$, and $R_7$ are either the same or different, each being selected from the group consisting of hydrogen and hydrocarbon residues of 1 to 10 carbon atoms;

$R_8$ is selected from the group consisting of hydrogen and hydrocarbon residues of 1 to 45 carbon atoms; and optionally, $R_4$ joining with $R_6$ and $R_7$, or $R_7$ joining with $R_6$ or $R_8$ to form an alicyclic ring or an oxygen-containing heterocyclic ring, which comprises heating an allylacetal of formula (I) in an inert organic solvent

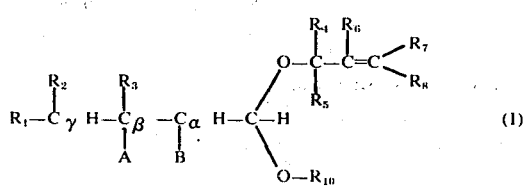

in which $R_1$, $R_2$, $R_3$, $R_4$, $R_5$, $R_6$, $R_7$, and $R_8$ have the same definitions as in formula (II);

$R_{10}$ is a member selected from the group consisting of

Table 20

| Run No. 13 Structure | B.P. °C/mmHg | High-mass data Calculated | Found | Infrared spectrum (specific absorption) | | NMR spectrum (specific absorption) | | |
|---|---|---|---|---|---|---|---|---|
| | | | | | | H(b) | τ value 4.04–4.38(m) | H number 1 |
| acetyl CH₃ O—CH₂—C=CH₂ CH₃—CH=CH—CH (d) (e) (c) (b) (a) O—CH₂—C=CH₂ [I] CH₃ 1,1-di-(2-methyl-2-propenyloxy)-2-butene | 62/0.2 | C₁₂H₂₀O₂ 196.1462 | C₁₂H₂₀O₂ 196.1432 | νC=C νC—O—C —C=CH₂ δCH | 1677 1658 1134 1110 1020 892 | H(a) H(e,c) H(d) | 4.50(d) 5.09–5.21(t) 6.16(s) | 1 5 4 |
| unsaturated carbonyl compound (b) (a) CH₃—CH=C—CHO CH(c) (d) CH₂=C [II] CH₃ 3-formyl-5-methyl-2,5-hexadiene C₈H₁₂O | 77/17 | C₈H₁₂O 124.0888 | C₈H₁₂O 124.0875 | C=C—CHO C=O —C=CH₂ δCH C=C νC=C | νC=O 1685 890 1645 | H9a) H(b) H(d) H(c) | 0.69(s) 3.24–3.46(m) 5.38(d) 7.05(s) | 1 1 2 2 |

We claim:

1. A process for the preparation of an unsaturated carbonyl compound of the formula (II)

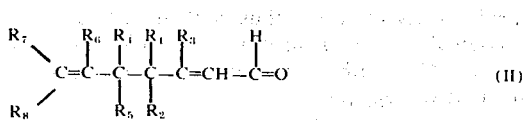

hydrogen, hydrocarbon residues of 1 to 20 carbons and carboxylic acid residues of 1 to 20 carbons;

A represents an alkoxy group or a carboxylic acid residue having 1 to 20 carbons; B represents hydrogen, at a temperature of 100° to 400°C. and separating the formed unsaturated carbonyl compound of formula (II) from the reaction mixture.

2. The process of claim 1 wherein $R_4$ in formula (II) joins with $R_6$ and $R_7$ to form an alicyclic ring or an oxygencontaining heterocyclic ring.

3. The process of claim 1 wherein $R_7$ in formula (II) joins with $R_6$ or $R_8$ to form an alicyclic ring or an oxygencontaining heterocyclic ring.

4. The process of claim 1 wherein the allylacetal of formula (I) is heated to a temperature of 130° to 400°C.

5. The process of claim 4 wherein the allylacetal of formula (I) is heated to a temperature of 150° to 350°C.

6. The process of claim 1 which includes carrying out the reaction in the presence of an acid catalyst having an acid strength, pKa, within the range of up to 10, the amount of the catalyst being no more than 500 mol % and no less than $1 \times 10^{-6}$ mol % per mole of the allylacetal of formula (I).

7. The process of claim 6 wherein the acid catalyst has an acid strength, pKa, of up to 7.

8. The process of claim 7 wherein the acid catalyst has an acid strength, pKa, of up to 5.

9. The process of claim 6 wherein the acid catalyst is present in an amount of not more than 250 mol % per mole of the allylacetal of formula (I).

10. The process of claim 9 wherein the acid catalyst is present in an amount of not more than 100 mol % per mole of the allylacetal of formula (I).

11. The process of claim 6 wherein the amount of acid catalyst present is not less than $1 \times 10^{-5}$ mol % per mole of the allylacetal of formula (I).

12. The process of claim 1 wherein the inert organic solvent is an aliphatic hydrocarbon having 1 to 20 carbon atoms.

13. The process of claim 1 wherein the inert organic solvent is an aromatic hydrocarbon having 1 to 20 carbon atoms.

* * * * *

UNITED STATES PATENT OFFICE
CERTIFICATE OF CORRECTION

Patent No. 3,978,092                Dated August 31, 1976

Inventor(s) Yataro Ichikawa et al.

It is certified that error appears in the above-identified patent and that said Letters Patent are hereby corrected as shown below:

Claim 1, formula (II), delete in its entirety and insert the following therefor:

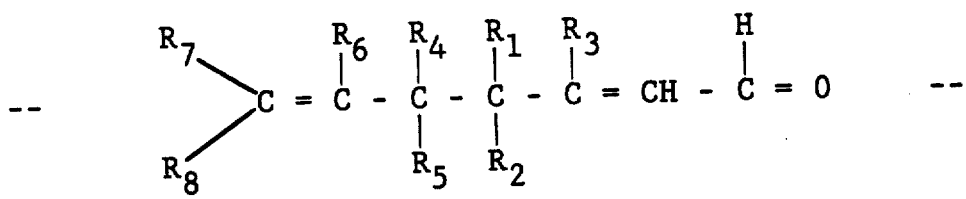

Claim 1, column 32, line 15, delete "and" in the second instance insert -- or --

Claim 1, column 33, line 4, after ";" insert -- and --

Signed and Sealed this

Eighteenth Day of October 1977

[SEAL]

Attest:

RUTH C. MASON  
Attesting Officer

LUTRELLE F. PARKER  
Acting Commissioner of Patents and Trademarks